(12) United States Patent
Papet et al.

(10) Patent No.: US 9,884,158 B2
(45) Date of Patent: Feb. 6, 2018

(54) MOLDED PART MADE OF A SYNTHETIC MATERIAL

(71) Applicant: APTAR FRANCE SAS, Le Neubourg (FR)

(72) Inventors: Gerard Papet, Sotteville les Rouen (FR); Anthony Saussaye, Menilles (FR)

(73) Assignee: APTAR FRANCE SAS, Le Neubourg (FR)

( * ) Notice: Subject to any disclaimer, the term of this patent is extended or adjusted under 35 U.S.C. 154(b) by 414 days.

(21) Appl. No.: 14/646,998

(22) PCT Filed: Dec. 11, 2013

(86) PCT No.: PCT/FR2013/053025
§ 371 (c)(1),
(2) Date: May 22, 2015

(87) PCT Pub. No.: WO2014/091150
PCT Pub. Date: Jun. 19, 2014

(65) Prior Publication Data
US 2015/0290405 A1   Oct. 15, 2015

(30) Foreign Application Priority Data

Dec. 11, 2012   (FR) .................................... 12 61890

(51) Int. Cl.
*A61M 15/00* (2006.01)
*G06M 1/08* (2006.01)
*B65D 83/16* (2006.01)
*G06M 3/00* (2006.01)
(Continued)

(52) U.S. Cl.
CPC ........ *A61M 15/007* (2014.02); *A61M 15/009* (2013.01); *A61M 15/0075* (2014.02); *B65D 83/16* (2013.01); *G06M 1/083* (2013.01); *G06M 3/00* (2013.01); *A61M 2207/00* (2013.01); *B05B 11/308* (2013.01); *B65D 83/386* (2013.01)

(58) Field of Classification Search
CPC ............ A61M 15/007; A61M 15/0075; A61M 15/009; A61M 2207/00; B65D 83/16; B65D 83/386; G06M 1/083; G06M 3/00; B05B 11/308
USPC ..................................................... 128/205.23
See application file for complete search history.

(56) References Cited

U.S. PATENT DOCUMENTS

2007/0029341 A1    2/2007  Stradella et al.

FOREIGN PATENT DOCUMENTS

| DE | 10 2011 005075 A1 | 9/2012 |
| FR | 2 533 895 A1 | 4/1984 |
| WO | 2005/017463 A2 | 2/2005 |

OTHER PUBLICATIONS

International Search Report for PCT/FR2013/053025 dated Apr. 29, 2014.
(Continued)

*Primary Examiner* — Andrew S Lo
(74) *Attorney, Agent, or Firm* — Sughrue Mion, PLLC

(57) ABSTRACT

A molded part that is made of synthetic material and that has a rigid frame and at least one movable portion that is movable and/or deformable relative to the rigid frame. The at least one movable portion is connected, during molding, to the rigid frame via at least one breakable bridge of material. The at least one breakable bridge of material is
(Continued)

broken while the molded part is being assembled, or while the molded part is being used for the first time.

8 Claims, 1 Drawing Sheet

(51) Int. Cl.
  *B05B 11/00* (2006.01)
  *B65D 83/38* (2006.01)

(56) References Cited

OTHER PUBLICATIONS

International Preliminary Report on Patentability dated Jun. 25, 2015, issued by the International Bureau of WIPO in counterpart International Application No. PCT/FR2013/053025.

MOLDED PART MADE OF A SYNTHETIC MATERIAL

CROSS REFERENCE TO RELATED APPLICATIONS

This application is a National Stage of International Application No. PCT/FR2013/053025, filed on Dec. 11, 2013, which claims priority from French Patent Application No. 12 61890, filed on Dec. 11, 2012, the contents of all of which are incorporated herein by reference in their entirety.

The present invention relates to a molded part made of synthetic material, and more particularly to an actuator for actuating a dose counter or indicator of a fluid dispenser device, such as an inhaler.

Counter actuators are complex parts that generally include at least one movable portion. The movable portion is moved or deformed during actuation, thereby driving a counter element of the counter. Since it is essential for dose counters to be reliable, in particular for devices that dispense drugs, such actuators must guarantee proper actuation of the counter each time the device is actuated. Document WO 2005/017463 describes such a dose counter or indicator.

Unfortunately, as with any molded-plastics part, there can be a risk of the movable portion(s) deforming, in particular on being unmolded, during transit and storage, and finally during assembly. In order to limit such risks, actuators are treated with special care, which increases, in particular, their manufacturing and packaging costs.

Documents DE 10 2011 005 075 and FR 2 533 895 describe prior-art devices.

An object of the present invention is to provide a molded part made of synthetic material, in particular an actuator for actuating a dose counter or indicator, that does not have the above-mentioned drawbacks.

In particular, an object of the present invention is to provide such a molded part made of synthetic material that is simple and inexpensive to manufacture and to assemble, and that can, in particular, be applied to any existing fluid dispenser device without requiring the assembly procedure to be modified.

The present invention thus provides a molded part that is made of synthetic material and that comprises a rigid frame and at least one movable portion that is movable and/or deformable relative to said rigid frame, said at least one movable portion being connected, during molding, to said rigid frame via at least one breakable bridge of material, said at least one breakable bridge of material being broken while said molded part is being assembled, or while said molded part is being used for the first time, said molded part being an actuator for actuating a dose counter or indicator of a fluid dispenser device, said actuator comprising a rigid frame and at least one flexible tab that pivots relative to said rigid frame, at least one bridge of material being formed between said rigid frame and said flexible tab.

Advantageously, said actuator includes a transmission element that is movable in translation relative to said rigid frame, and that is adapted to co-operate with a portion of said dispenser device each time said device is actuated.

Advantageously, said flexible tab includes a first flexible tab portion and a second flexible tab portion that is more rigid than the first flexible tab portion, the first tab portion supporting an actuator tooth and the second tab portion supporting the transmission element.

Advantageously, said second flexible tab portion comprises two branches that form an oval structure having two opposite ends that are formed firstly by the transmission element, and secondly by a junction with the first flexible tab portion, said oval structure being capable of stretching by moving said transmission element, and of returning resiliently to its rest position when the transmission element is no longer stressed.

Advantageously, at least one bridge of material is formed between said rigid frame and said second flexible tab portion and/or said transmission element of said flexible tab.

The present invention also provides a dose indicator for a fluid dispenser device, said dose indicator including an actuator as described above.

The present invention also provides a fluid dispenser device comprising a fluid reservoir and a dispenser member, such as a pump or a valve, mounted on said reservoir, said device including such a dose indicator.

Advantageously, said at least one breakable bridge is broken while said actuator is being assembled, or while said dispenser device is being actuated for the first time.

Other characteristics and advantages of the present invention appear more clearly from the following detailed description of a particular embodiment thereof, given by way of non-limiting example, and with reference to the accompanying drawing, in which.

The present invention applies to any type of molded part that is made of synthetic material and that is provided with at least one flexible element, such as an elastically-deformable tab, that is secured to a stationary structure. However, the following description is made with reference, more precisely, to a particular actuator for actuating a dose indicator for a fluid dispenser device. However, it is understood that the present invention is not limited to such an actuator.

Figure 1:
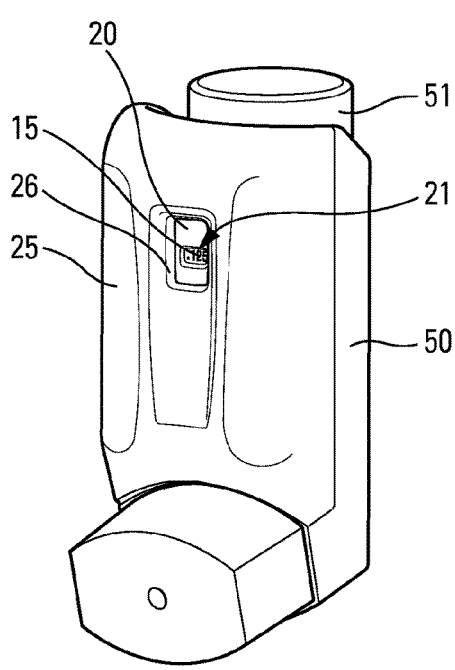
FIG. 1 is a diagrammatic perspective view of a fluid dispenser device to which the present invention may apply.
Figure 2:
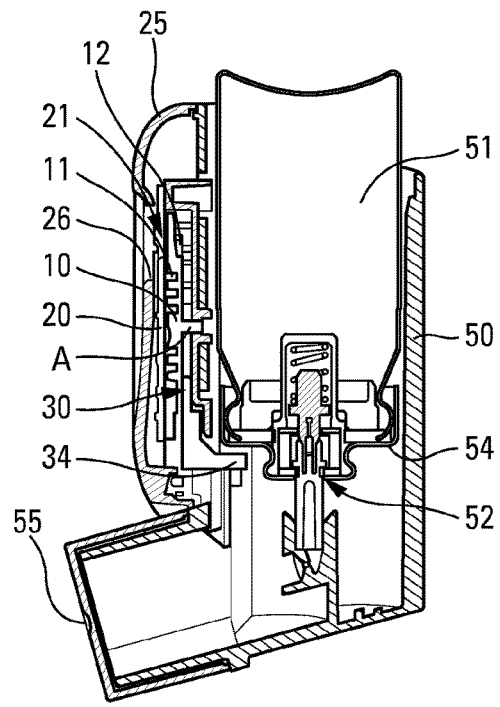
FIG. 2 is a longitudinal-section side view of the FIG. 1 device.

FIGS. 1 and 2 are diagrams showing a dispenser device to which the present invention applies more particularly. This inhaler device comprises a body 50 and a reservoir 51 on which a metering valve 52 is assembled. The device is actuated by moving the reservoir 51 axially inside the body 50, such movement causing the valve member of the valve 52 to compress, and this causes a dose of fluid to be expelled through a mouthpiece 55. Naturally, the present invention also applies to other types of dispenser device, and in particular spray devices of the nasal type, or devices including a pump to replace the valve.

The dispenser device includes a dose indicator that comprises at least one rotary counter means 10. In the embodiment shown, the counter means are formed by a rotary counter disk that is adapted to turn about a pivot pin A that is substantially perpendicular to said disk. The rotary disk is preferably thin and is provided with a hollow profile 11 that may advantageously be formed by means of a rib or groove. Advantageously, the disk further includes a set of teeth 12, preferably formed on its periphery, said set of teeth being adapted to co-operate with an actuator 30 that is adapted to turn said disk, and that is described more fully below. The counter disk or wheel also includes indicator means 15 that may be numbers and/or symbols, and that are for indicating the number of doses that have been dispensed or that remain to be dispensed, as can be seen in FIG. 1. Naturally, the present invention also applies to different dose counters or indicators.

Advantageously, the indicator shown in FIG. 2 may also include a member 20 that is adapted to move in translation. The member that is movable in translation may include a projection, or any other equivalent means, that co-operates with said hollow profile 11 of the rotary disk 10. The member 20 that is movable in translation is preferably made in the form of a thin plate, and includes a viewing slot 21 for co-operating with the indicator means of the rotary disk.

Given the shape of the hollow profile 11, a turning movement of the counter wheel 10 causes the member 20 to move in translation. Advantageously, the counter wheel and the member that is movable in translation are arranged in a cover 25 that, preferably, is also thin in structure, and that includes a viewing window 26 that co-operates with the viewing slot 21 of the member that is movable in translation, so as to enable the user to view the indicator means of the counter wheel 10.

The indicator may advantageously be actuated, and in particular the rotary counter wheel 10 turned, by an actuator 30 of said indicator.

Figure 3:
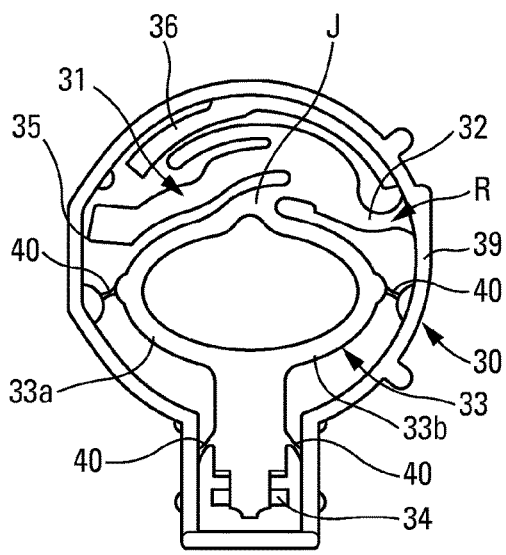
FIG. 3 is a diagrammatic front view of an actuator in an advantageous embodiment of the invention, in its storage position.
Figure 4:
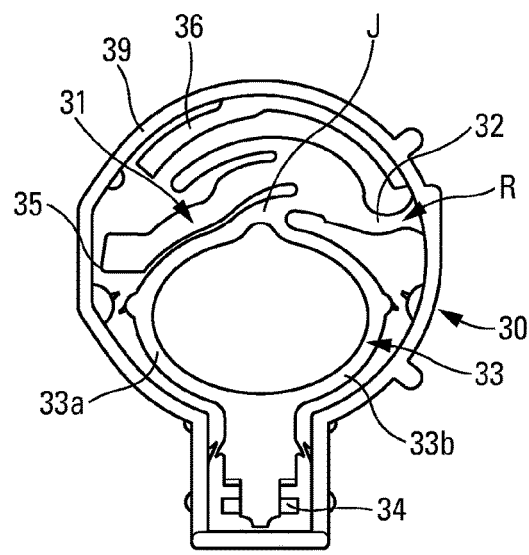
FIG. 4 is a view similar to the view in FIG. 3, in the actuated position.

FIGS. 3 and 4 show an actuator 30 that is adapted to the device in FIGS. 1 and 2. Similar to the actuator described in document WO 2005/017463, the actuator 30 may advantageously include a drive element that is made in the form of a flexible tab 31 that is secured to a rigid frame 39. Each time a dose is dispensed, the flexible tab 31 is adapted to co-operate with said set of teeth, preferably by means of a tooth 35. Advantageously, non-return means 36 are provided to prevent said rotary disk 10 from turning in the direction opposite to the direction that is imparted thereto by the flexible tab 31 during actuation. The non-return means may comprise a flexible tab 36 that supports a non-return tooth that co-operate with the set of teeth.

The actuator 30 also includes a transmission element 34 that is adapted to co-operate with the fluid dispenser device each time said device is actuated, said transmission element 34 also co-operating with said flexible tab 31 so as to turn said rotary disk 10. In particular, said transmission element 34 is a shoulder that co-operates with a portion 54 of the fluid dispenser device that is movable during actuation. In the embodiment shown, said portion is the fastener ring 54 for fastening the metering valve 52 on the reservoir 51. Naturally, and more generally, any portion that moves while the device is being actuated is suitable for co-operating with the shoulder 34, so as to actuate the dose indicator.

Advantageously, the flexible tab 31 may be provided with two flexible portions 32 and 33 of different flexibilities, the first portion 32 being more flexible than the second portion 33. The second tab portion 33 supports said shoulder 34, and when the dispenser device is actuated, the fastener ring 54 of the reservoir firstly causes the more flexible portion 32 of the arm 31 to flex, thereby causing said counter disk to turn by means of the actuator tooth 35 that co-operates with the set of teeth. Thus, during actuation, the shoulder 34 is moved downwards in translation (in the position shown in FIGS. 3 and 4) by the dispenser device, and the more flexible arm portion 32 flexes, causing the flexible tab 31 to pivot. This causes the counter wheel to turn over the equivalent of one tooth of the set of teeth 11. The more flexible first tab portion 32 is thus blocked, and the actuation stroke of the dispenser device may continue by flexing the less flexible tab portion 33. In this way, it is possible to actuate the dose indicator in the first portion of said actuation stroke. This eliminates any risk of failing to count a dose that has been dispensed (whether completely, or in part only), while enabling the actuation stroke to continue after counting.

Advantageously, amplification means are provided that are adapted to amplify the movement of the transmission element 34 at the very start of the actuation stroke, so that the movement of the tooth 35 is greater than the movement of said transmission element 34. In the embodiment shown, the second tab portion 33 advantageously comprises two branches 33a and 33b. The branches are preferably convex, and they are fastened firstly to the first tab portion 32 at a junction J, and secondly to the transmission element 34. As can be seen in FIGS. 3 and 4, the branches 33a and 33b may form an oval structure with two opposite top and bottom ends, one formed by said junction J, the other formed by said transmission element 34. Movement of the transmission element 34 thus causes the oval structure to stretch, pulling on the first tab portion 32. At the start of the actuation stroke, the transmission element 34 is moved downwards in FIG. 3. The transmission element 34, and thus the second tab portion 33, move in translation, without deforming the second tab portion 33, which is more rigid. Only the more flexible first tab portion 32 is moved in turning. Since the junction J is in alignment with the transmission element, said junction J performs the same movement in translation as said transmission element 34 at the start of actuation, while the second tab portion 33 does not deform. Consequently, since the junction J is offset relative to the turning axis R of the first tab portion 32, and since the tooth 35 is situated on the other side of the junction J relative to the turning axis R, the movement of the tooth 35 is amplified relative to the movement of the junction J. In this embodiment, when the junction is approximately at the center of the first tab portion 32, the amplification factor is approximately 2. Naturally, by modifying the position of the junction J, it is possible to modify the amplification factor, knowing that it will always be greater than 1. Advantageously, the branches 33a and 33b return resiliently to their rest position after actuation.

Naturally, the resilient structure having two convex branches could be replaced by any single-branch or multi-branch structure of any shape. The essential point for this particular actuator is that the structure is fastened to the first tab portion 32, and that it is elastically deformable firstly for causing the first tab portion to turn at the start of the actuation stroke, and secondly for enabling the actuation stroke to continue to the end of its stroke.

It should thus be observed that this type of actuator must be particularly accurate and reliable so as to avoid any malfunctioning of the indicator. It is thus desirable to prevent, as much as possible, any risk of the flexible portions of said actuator deforming before it is used, and in particular during its manufacture, its storage, its transit, and its assembly.

In the present invention, provision is thus made to fasten the movable portions of the actuator to the rigid ring 39 of said actuator by means of at least one breakable bridge of material 40. Thus, at least one bridge of material 40 is formed between said rigid frame 39 and said flexible tab 31. Advantageously, the bridge of material 40 is formed at said second flexible tab portion 33 and/or at said transmission element 34. Advantageously, a plurality of bridges of material may be provided, e.g. four, as shown in FIG. 3.

Thus, during molding, the transmission element 34 and the branches 33a and 33b may be fastened to the rigid frame 39, thereby preventing any deformation of the flexible and/or deformable portions relative to said frame, whether this be a movement in translation, in pivoting, or in warping out of the plane of the actuator. Naturally, the bridge(s) of material may be provided at any appropriate location(s) of the actuator.

In order to use the actuator, the simplest solution is to break the bridges of material while the device is being actuated for the first time. The force exerted by the user to move the reservoir 51 into the body 50 and thus to actuate the valve 52 then needs to be sufficient to break the bridge(s) of material 40. With this assumption, the presence of the bridges of material does not modify the procedure for assembling the actuator, and this is particularly advantageous.

In a variant, the bridges of material 40 may be cut during assembly of the dose indicator. Specifically, once assembled in the indicator, any risk of deforming the actuator 30 is much lower than during the preceding stages of manufacturing, storing, or transporting it.

Any appropriate cutting means can be envisaged, such as laser cutting, for example. This makes assembling the actuator a little more complex, but this may be justified in some circumstances.

The present invention thus makes it possible, in particular, to obtain the following advantages:
- to eliminate deformation of the flexible elements of the actuator while it is being molded, and in particular after it has been ejected from the mold;
- to eliminate potential deformation as a result of handling, transferring, and packaging the actuator after molding;
- to reduce the costs of packaging and storage, and to simplify operations; and
- to improve the robustness of the method of assembling the indicator, in particular the actuator.

More generally, the present invention relates to any molded part that includes at least one portion that is movable and/or deformable relative to a rigid portion, and proposes limiting or preventing any deformation of said flexible portion before it is assembled and/or before it is used for the first time.

The present invention is described above with reference to a particular embodiment, as shown in the drawings, but it is not limited to this particular embodiment. On the contrary, any modification could be applied thereto by a person skilled in the art, without going beyond the ambit of the present invention, as defined in the accompanying claims.

The invention claimed is:

1. A molded part that is made of synthetic material and that comprises a rigid frame and at least one movable portion that is movable and/or deformable relative to said rigid frame, said at least one movable portion being connected, during molding, to said rigid frame via at least one breakable bridge of material, said at least one breakable bridge of material configured to be broken while said molded part is being assembled, or while said molded part is being used for the first time, said molded part being characterized in that it is an actuator for actuating a dose counter or indicator of a fluid dispenser device, said actuator comprising a rigid frame and at least one flexible tab that pivots relative to said rigid frame, at least one bridge of material being formed between said rigid frame and said flexible tab.

2. The molded part according to claim 1, wherein said actuator includes a transmission element that is movable in translation relative to said rigid frame, and that is adapted to co-operate with a portion of said dispenser device each time said dispenser device is actuated.

3. The molded part according to claim 1, wherein said flexible tab includes a first flexible tab portion and a second flexible tab portion that is more rigid than the first flexible tab portion, the first tab portion supporting an actuator tooth and the second tab portion supporting the transmission element.

4. The molded part according to claim 3, wherein said second flexible tab portion comprises two branches that form an oval structure having two opposite ends that are formed firstly by the transmission element and secondly by a junction with the first flexible tab portion, said oval structure being capable of stretching by moving said transmission element, and of returning resiliently to its rest position when the transmission element is no longer stressed.

5. The molded part according to claim 3, wherein at least one bridge of material is formed between said rigid frame and said second flexible tab portion and/or said transmission element of said flexible tab.

6. A dose indicator for a fluid dispenser device, said dose indicator being characterized in that it includes an actuator according to claim 1.

7. A fluid dispenser device comprising a fluid reservoir and a dispenser member including a pump or a valve, mounted on said reservoir, said dispenser device being characterized in that it includes a dose indicator according to claim 6.

8. The device according to claim 7, wherein said at least one breakable of material bridge is broken while said actuator is being assembled, or while said dispenser device is being actuated for the first time.

* * * * *